(12) United States Patent
Dong (10) Patent No.: US 11,216,068 B2
(45) Date of Patent: Jan. 4, 2022

(54) DETECTION DEVICE AND DETECTION METHOD

(71) Applicant: BOE TECHNOLOGY GROUP CO., LTD., Beijing (CN)

(72) Inventor: Wenchu Dong, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 878 days.

(21) Appl. No.: 15/779,051

(22) PCT Filed: Oct. 26, 2017

(86) PCT No.: PCT/CN2017/107732
§ 371 (c)(1),
(2) Date: May 24, 2018

(87) PCT Pub. No.: WO2018/205505
PCT Pub. Date: Nov. 15, 2018

(65) Prior Publication Data
US 2021/0165487 A1  Jun. 3, 2021

(30) Foreign Application Priority Data

May 11, 2017 (CN) .......................... 201710329277.2

(51) Int. Cl.
*G06F 3/01* (2006.01)
*A61B 5/381* (2021.01)
(Continued)

(52) U.S. Cl.
CPC .............. *G06F 3/015* (2013.01); *A61B 5/381* (2021.01); *A61B 5/486* (2013.01); *A61B 5/72* (2013.01);
(Continued)

(58) Field of Classification Search
CPC ......... G06F 3/015; A61B 5/381; A61B 5/486; A61B 5/72; A61B 5/7276; G06K 9/00973; G06K 9/6256; G06K 2009/00939
See application file for complete search history.

(56) References Cited

U.S. PATENT DOCUMENTS

2005/0022034 A1* 1/2005 Chaudhari .............. G06F 21/32
726/19
2005/0085744 A1  4/2005 Beverina et al.
(Continued)

FOREIGN PATENT DOCUMENTS

CN          1865996 A    11/2006
CN       103210411 A     7/2013
(Continued)

OTHER PUBLICATIONS

Lledo et al. 'Information Processing in the Mammalian Olfactory System' Physiol Rev 85: 281-317, 2005; doi:10.1152/physrev.00008. 2004. (Year: 2005).*

(Continued)

*Primary Examiner* — Patrick Fernandes
(74) *Attorney, Agent, or Firm* — Kinney & Lange, P.A.

(57) ABSTRACT

The present disclosure relates to the field of brainwave technology, and provides a detection device and a detection method. The detection device includes: a brainwave acquisition circuit configured to collect a brainwave signal of a user in the case that a distance between the user and a to-be-detected object is smaller than a threshold; and a processing circuit configured to process the collected brainwave signal to acquire brainwave information, and acquire a detection result of the to-be-detected object in accordance (Continued)

with the brainwave information. The brainwave information includes at least one of olfactory information and gustatory information of the user.

17 Claims, 4 Drawing Sheets

(51) Int. Cl.
*A61B 5/00* (2006.01)
*G06K 9/00* (2006.01)
*G06K 9/62* (2006.01)

(52) U.S. Cl.
CPC ........ *A61B 5/7267* (2013.01); *G06K 9/00973* (2013.01); *G06K 9/6256* (2013.01); *G06K 2009/00939* (2013.01)

(56) References Cited

U.S. PATENT DOCUMENTS

| | | | |
|---|---|---|---|
| 2013/0191393 A1 | 7/2013 | Ji | |
| 2015/0112161 A1* | 4/2015 | Mills | A61B 5/4088 600/303 |

FOREIGN PATENT DOCUMENTS

| | | |
|---|---|---|
| CN | 103699230 A | 4/2014 |
| CN | 104281264 A | 1/2015 |
| CN | 104888332 A | 9/2015 |
| CN | 106502409 A | 3/2017 |
| CN | 107015660 A | 8/2017 |
| CN | 101464729 A | 3/2018 |

OTHER PUBLICATIONS

Robinson et al. 'Olfaction Modulates Early Neural Responses to Matching Visual Objects' Journal of Cognitive Neuroscience 27:4, pp. 832-841 doi:10.1162/jocn_a_00732 (Year: 2015).*
Yan, Liang; Scent of Things; Life World, No. 5, 2004, ISSN 1673-0437; pp. 6-7, with paragraphs 5 and 6 on p. 6 translated into English (May 31, 2004), 3 total pages.
International Search Report & English Translation of Box V of the Written Opinion, for PCT Patent Application No. PCT/CN2017/107732, dated Feb. 13, 2018, 12 pages.
First Chinese Office Action dated Feb. 28, 2019, received for corresponding Chinese Application No. 201710329277.2.

* cited by examiner

DETECTION DEVICE AND DETECTION METHOD

CROSS-REFERENCE TO RELATED APPLICATION

The present application is the U.S. national phase of PCT Application No. PCT/CN2017/107732 filed on Oct. 26, 2017, which claims a priority of the Chinese patent application No. 201710329277.2 filed on May 11, 2017, which is incorporated herein by reference in its entirety.

BACKGROUND

The present disclosure relates generally to the field of brainwave technology, and more specifically to a detection device and a detection method.

In the 1980s, two American scientists, Linda B. Buck and Richard Axel, worked together to investigate the functioning of the olfactory system. They found that different odor receptors are distributed on a cell membrane of a human nasal cavity, and 3% of the total number of human genes (i.e., about 1000 genes) are used to code odor receptors so as to differentiate different odors. Although humans have only about 1000 odor receptors, these can be combined in a huge number of ways, so as to form a huge number of distinct odor patterns. On this basis, a person can be capable of differentiating and memorizing about 10,000 odors. Odorant molecules may be bound to the odor receptors located in epithelial odor receptor cells of the nose. After these odor receptors are activated by the odorant molecules, electrical signals can be generated by the odor receptor cells, then transmitted to a small region of the brain where olfactory bulbs are located, and then transmitted to the other regions of the brain so as to form a specific pattern. In this way, the person may consciously sense an odor (e.g., the smell of jasmine), and remember this odor at another time.

In addition, the human olfactory system is highly specialized. For example, each odor receptor cell only expresses one kind of olfactory receptor gene, and the number of kinds of odor reception cells are the same as the number of kinds of the odor receptors. A neural signal may be transmitted by the odor receptor cell to a micro structure of the olfactory bulb in the brain called an "olfactory glomeruli," There are about 2000 glomeruli in the human brain, i.e., the number of the glomeruli is double the number of kinds of odor reception cells. The olfactory glomeruli is also highly specialized, and neutral signals are transmitted by odor receptor cells carrying the same receptors to the corresponding olfactory glomeruli, i.e., information derived from the cells having the same receptor may be collected by the corresponding olfactory glomeruli. A neutral cell called a mitral cell is subsequently activated by the olfactory glomeruli, and each mitral cell is only activated by each olfactory glomeruli, so as to maintain the speciality of the information transmission in the olfactory system continuously. Next, the information is transmitted by the mitral cell to other portions of the brain. In this way, the information derived from different kinds of odor receptors may be combined into a pattern corresponding to a particular odor, and the brain is able to consciously that odor.

Apart from the mechanism of human olfactory function, Buck and Axel discovered that the brains of other animals are also capable of consciously sensing specific odors. For example, rats are trained in such a manner as to search for people buried under the debris after an earthquake. To be specific, the rat is macrosmatic, and after being trained for several months, it may remember the human odor. An electrode can be implanted into the rat's brain and connected to an electronic transmitter. If the rat senses the odor of a target, its brainwave diagram can express such information as "aha, I've got it". Based on this signal, it is possible to determine a position of the rat, i.e., a position of the trapped person.

Along with the development of brainwave detection and analysis technology, the above scientific achievement has a great theoretical value, and is relevant to a wide range of applications.

SUMMARY

In one aspect, the present disclosure provides in some embodiments a detection device, including: a brainwave acquisition circuit configured to collect a brainwave signal of a user in the case that a distance between the user and a to-be-detected object is smaller than a threshold; and a processing circuit configured to process the collected brainwave signal to acquire brainwave information, and acquire a detection result of the to-be-detected object in accordance with the brainwave information. The brainwave information includes at least one of olfactory information and gustatory information of the user.

In a possible embodiment of the present disclosure, the detection device further includes an image collection circuit in communication with the processing circuit and configured to collect image data about the to-be-detected object. The processing circuit is further configured to process the image data collected by the image collection circuit to acquire visual information about the to-be-detected object, and acquire the detection result of the to-be-detected object in accordance with the visual information and the brainwave information.

In a possible embodiment of the present disclosure, the detection device further includes a storage device configured to store therein a detection model. The processing circuit is further configured to input the visual information and the brainwave information into the detection model, so as to acquire the detection result of the to-be-detected object.

In a possible embodiment of the present disclosure, the detection device further includes a detection model generation circuit configured to: acquire training data, the training data including a plurality of detection results and a feature of the detection model corresponding to each detection result, the feature including olfactory neuron brainwave information, gustatory neuron brainwave information and visual information of the user collected in the case that the distance between the user and the to-be-detected object is smaller than the threshold; estimate a weight value of the feature of the detection model in accordance with the training data; and generate the detection model in accordance with the estimated weight value.

In a possible embodiment of the present disclosure, the image collection circuit includes: a light transmitter configured to transmit a light beam toward the to-be-detected object; and an optical processor configured to detect at least one of a light beam acquired after the light beam from the light transmitter passes through the to-be-detected object and a light beam acquired after the light beam from the light transmitter is reflected by the to-be-detected object, so as to acquire the visual information about the to-be-detected object.

In a possible embodiment of the present disclosure, the brainwave acquisition circuit includes a frame and a plurality of detection electrodes arranged on the frame.

In a possible embodiment of the present disclosure, the image collection circuit is arranged on the frame and connected in a wired or wireless manner to the processing circuit.

In a possible embodiment of the present disclosure, the detection device further includes a prompting circuit configured to send a prompt to the user after the image data about the to-be-detected object has been collected by the image collection circuit.

In a possible embodiment of the present disclosure, the detection device further includes a display device configured to display the visual information about the to-be-detected object.

In another aspect, the present disclosure provides in some embodiments a detection method, including steps of: collecting a brainwave signal of a user in the case that a distance between the user and a to-be-detected object is smaller than a threshold; and processing the collected brainwave signal to acquire brainwave information and acquiring a detection result of the to-be-detected object in accordance with the brainwave information. The brainwave information includes at least one of olfactory information and gustatory information of the user.

In a possible embodiment of the present disclosure, the detection method further includes: collecting image data about the to-be-detected object; and processing the image data to acquire visual information about the to-be-detected object, and acquiring the detection result of the to-be-detected object in accordance with the visual information and the brainwave information.

In a possible embodiment of the present disclosure, the step of acquiring the detection result of the to-be-detected object in accordance with the visual information and the brainwave information includes inputting the visual information and the brainwave information into a detection model acquired in advance, so as to acquire the detection result of the to-be-detected object.

In a possible embodiment of the present disclosure, the detection method further includes a step of generating the detection model, and the step of generating the detection model includes: acquiring training data, the training data including a plurality of detection results and a feature of the detection model corresponding to each detection result, the feature including olfactory neuron brainwave information, gustatory neuron brainwave information and visual information of the user collected in the case that the distance between the user and the to-be-detected object is smaller than the threshold; estimating a weight value of the feature of the detection model in accordance with the training data; and generating the detection model in accordance with the estimated weight value.

In yet another aspect, the present disclosure provides in some embodiments a detection device realized by a computer, the computer including a processor, a memory, and a computer program stored in the memory and configured to be executed by the processor so as to implement the above-mentioned method.

In still yet another aspect, the present disclosure provides in some embodiments a computer-readable storage medium storing therein a computer program which is executed by a processor so as to implement the above-mentioned method.

BRIEF DESCRIPTION OF THE DRAWINGS

In order to illustrate the technical solutions of the present disclosure or the related art in a clearer manner, the drawings desired for the present disclosure or the related art will be briefly described hereinafter. The following drawings merely relate to some embodiments of the present disclosure, and based on these drawings, a person skilled in the art may obtain the other embodiments without creative effort.

DETAILED DESCRIPTION

The present disclosure will be described hereinafter in conjunction with the drawings and embodiments. The following embodiments are for illustrative purposes only, and should not be construed to limit the scope of the present disclosure.

In order to make the objects, the technical solutions and the advantages of the present disclosure more apparent, the present disclosure will be described hereinafter in a clear and complete manner in conjunction with the drawings and embodiments. The following embodiments merely relate to a part of, rather than all of, the embodiments of the present disclosure, and based on these embodiments, a person skilled in the art may, without any creative effort, obtain other embodiments that also fall within the scope of the present disclosure.

An object of the present disclosure is to provide a detection device and a detection method, so as to detect a to-be-detected object on the basis of a detected brainwave.

Figure 1:
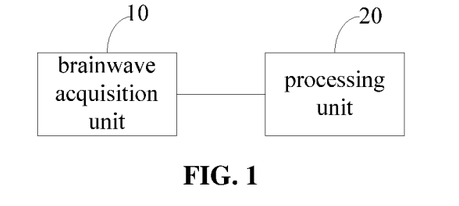
FIG. 1 is a schematic view showing a detection device according to at least one embodiment of the present disclosure.

The present disclosure provides in some embodiments a detection device which, as shown in FIG. 1, includes: a brainwave acquisition circuit 10 configured to collect a brainwave signal of a user in the case that a distance between the user and a to-be-detected object is smaller than a threshold; and a processing circuit 20 configured to process the collected brainwave signal to acquire brainwave information, and acquire a detection result of the to-be-detected object in accordance with the brainwave information. The brainwave information includes at least one of olfactory information and gustatory information of the user. The threshold may be set as 5 to 10 cm.

According to the detection device in the embodiments of the present disclosure, the brainwave signal of the user is collected in the case that the distance between the user and the to-be-detected object is smaller than the threshold, and the collected brainwave signal is then processed so as to acquire the brainwave information. The detection result of the to-be-detected object is acquired in accordance with the brainwave information. As a result, it is possible to acquire the detection result of the to-be-detected object immediately after the user wearing the detection device moves close to the to-be-detected object.

The brainwave signal can include, but is not limited to, an olfactory signal and a gustatory signal. The brainwave signal can include any other kinds of feasible signals contemplated by skilled person in the art, which will not be elaborated on herein.

In the case that the to-be-detected object is a liquid, different brainwaves of the user may be acquired due to different influences of different liquids on the olfaction or gustation. The brainwave signal of the user may be processed by the processing circuit so as to acquire the brainwave information, thereby to acquire the detection result of the to-be-detected object. The detection result may include an odor type and viscosity of the to-be-detected object. For example, it is possible to detect the liquid such as wine or liquor, so as to acquire an odor type, a vintage, and an alcohol content of the wine or liquor. In addition, the user may not necessarily be a specialized sommelier, but rather an ordinary person or a macrosmatic or taste-sensitive animal.

Figure 2:
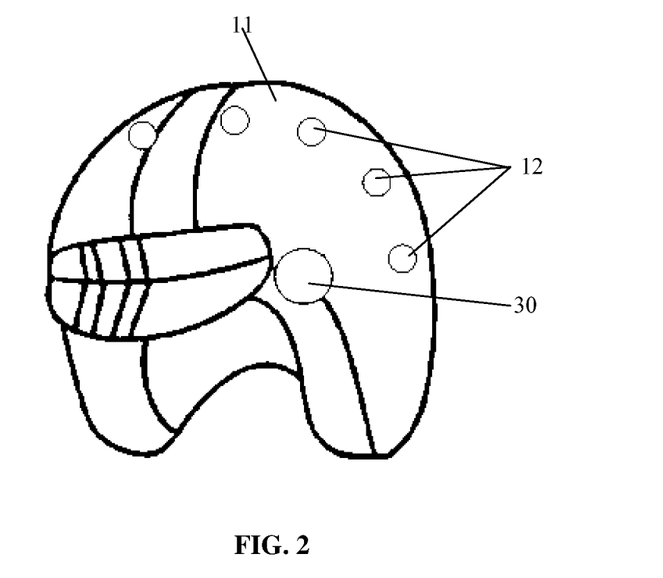
FIG. 2 is a schematic view showing a brainwave acquisition circuit according to at least one embodiment of the present disclosure.

To be specific, as shown in FIG. 2, the brainwave acquisition circuit 10 includes a frame 11, and a plurality of detection electrodes 12 arranged on the frame 11. In the case that the detection electrodes 12 are in contact with a head of the user, it is able to collect the brainwave signal of the user.

Olfactory neurons and gustatory neurons are distributed at different regions of the brain. Depending on the positions of olfactory neurons and gustatory neurons, the detection electrodes 12 may be distributed on frame 11 in such a manner as to detect the olfactory signal and the gustatory signal.

Frame 11 can be a helmet or a head-mounted bracket. In addition, frame 11 may be modified appropriately, e.g., its radian may be adjusted or an additional belt for fixation may be provided, so as to enable the frame to be adapted to different users. Further, the user may be a person, or an animal having a better olfactory or gustatory system, e.g., dog.

In a possible embodiment of the present disclosure, the detection device further includes an image collection circuit 30 in communication with processing circuit 20 and configured to collect image data about the to-be-detected object. Processing circuit 20 is further configured to process the image data collected by image collection circuit 30 to acquire visual information about the to-be-detected object, and to acquire the detection result of the to-be-detected object in accordance with the visual information and the brainwave information.

As shown in FIG. 2, image collection circuit 30 may be arranged on frame 11 and connected in a wired or wireless manner to processing circuit 20. In a possible embodiment of the present disclosure, image collection circuit 30 may not be arranged on the frame but instead connected in a wireless manner to processing circuit 20. In the case that image collection circuit 30 is connected in a wireless manner to processing circuit 20, remote communication between image collection circuit 30 and processing circuit 20 may be achieved through signal transmission.

Figure 8:
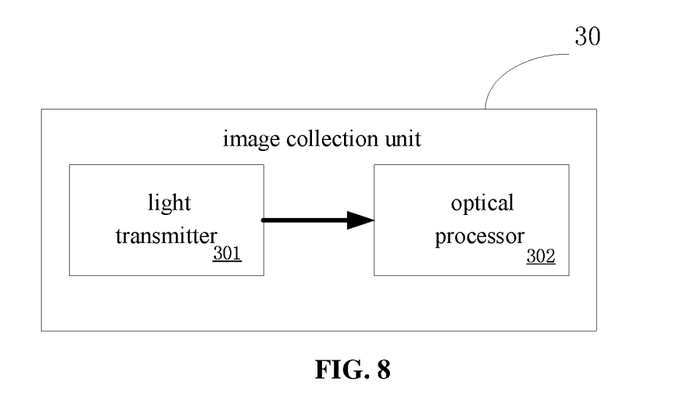
FIG. 8 is a block diagram of an image collection circuit according to at least one embodiment of the present disclosure.

To be specific, as shown in FIG. 8, image collection circuit 30 may include: a light transmitter 301 configured to transmit a light beam toward the to-be-detected object; and an optical processor 302 configured to detect at least one of a light beam acquired after the light beam from the light transmitter passes through the to-be-detected object and a light beam acquired after the light beam from the light transmitter is reflected by the to-be-detected object, so as to acquire the visual information about the to-be-detected object.

To be specific, the optical processor 302 of the image collection circuit 30 may be a charge coupled device (CCD) type image sensor. After the light beam is generated by the light transmitted toward the to-be-detected object, the CCD may detect at least one of the light beam acquired after the light beam from light transmitter 301 passes through the to-be-detected object and the light beam acquired after the light beam from light transmitter 301 is reflected by the to-be-detected object, so as to acquire at least one of a color value and a transparency value of the to-be-detected object.

To be specific, a detection model may be established in advance, and a feature of the detection model may include the visual information about the to-be-detected object and the brainwave information of the user. The visual information and the brainwave information may be inputted into the detection model, so as to acquire to the detection result of the to-be-detected object.

Figure 3:
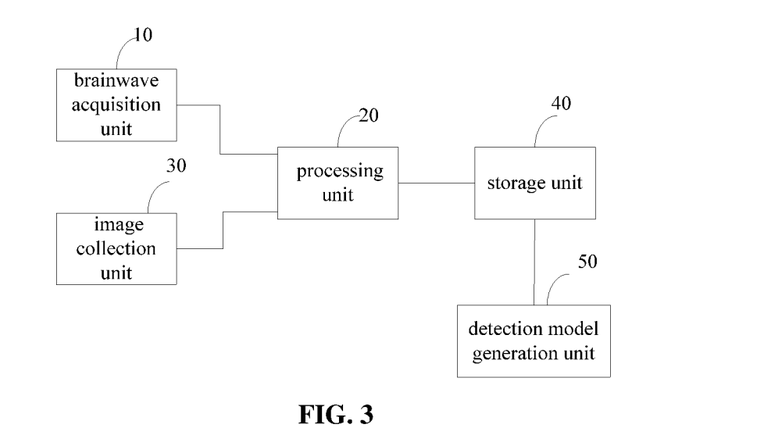
FIG. 3 is another schematic view showing the detection device according to at least one embodiment of the present disclosure.

In a possible embodiment of the present disclosure, as shown in FIG. 3, the detection device further includes a storage device 40 configured to store therein the detection model. The feature of the detection model may include the visual information about the to-be-detected object and the brainwave information of the user. The visual information and the brainwave information may be inputted into the detection model, so as to acquire the detection result of the to-be-detected object. Processing circuit 20 may be further configured to input the visual information and the brainwave information into the detection model, so as to acquire the detection result of the to-be-detected object.

In a possible embodiment of the present disclosure, as shown in FIG. 3, the detection device further includes a detection model generation circuit 50 configured to: acquire training data, the training data including a plurality of detection results and a feature of the detection model corresponding to each detection result, the feature including olfactory neuron brainwave information, gustatory neuron brainwave information and visual information of the user collected in the case that the distance between the user and the to-be-detected object is smaller than the threshold; estimate a weight value of the feature of the detection model in accordance with the training data; and generate the detection model in accordance with the estimated weight value.

During the implementation, in the case that the to-be-detected object is wine, the detection module may be expressed through the following equation:

$$p(\text{quality}|\text{parameter}) = \alpha_1 \times p_1(\text{quality}|\text{parameter}) + \alpha_2 \times p_2(\text{quality}|\text{parameter}) + \alpha_3 \times p_3(\text{quality}|\text{parameter}) \qquad (1)$$

where p represents the detection result (the detection result may be mapped onto a wine quality parameter table acquired in advance, and the wine quality parameter table may include such parameters as odor types, vintages and alcohol contents, i.e., it is able to obtain the parameters of the wine directly through the detection result), $p_1$ represents a value of the olfactory neuron brainwave information acquired through extracting and analyzing an olfactory neuron brainwave signal, $p_2$ represents a value of the gustatory neuron brainwave information acquired through extracting and analyzing a gustatory neuron brainwave signal, $p_3$ represents a value of the visual information acquired through analyzing the image data collected by the image collection circuit (including the color value, the transparency value and the viscosity of the wine), $\alpha_1$ represents a weight value of $p_1$, $\alpha_2$ is a weight value of $p_2$, $\alpha_3$ is a weight value of $p_3$. $\alpha_1$, $\alpha_2$ and $\alpha_3$ are used to adjust influence coefficients of $p_1$, $p_2$ and $p_3$ respectively, and their values vary with the individual and are acquired by a particular subject through multiple trainings. For example, after a specific sommelier has smelt and tasted different types of wines for many times, the detection results and the values of $p_1$, $p_2$ and $p_3$ corresponding to each detection result may be recorded, so as to acquire a plurality of sets of training data. Then, the values of $\alpha_1$, $\alpha_2$ and $\alpha_3$ of the detection model may be estimated in accordance with training data, and the detection model may be generated in accordance with the estimated weight values. In order to improve the accuracy of the detection model, a huge number of training data acquired by a plurality of sommeliers may be used to train the detection model. The more the training data and the larger the number of sommeliers, the more precise the detection model becomes.

Different detection models may be established with respect to different to-be-detected objects. In the case that the to-be-detected object is not wine, a huge number of training data may be acquired again, so as to train the detection model and estimate the weight values of the features of the detection model.

Figure 4:
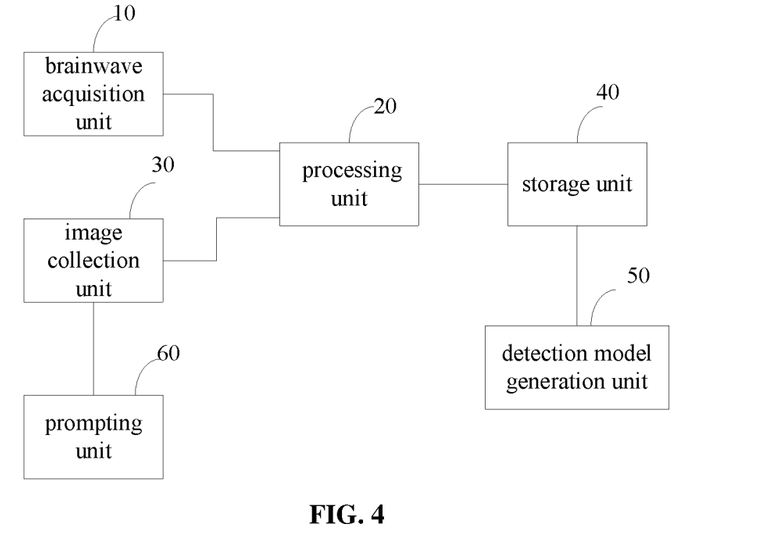
FIG. 4 is yet another schematic view showing the detection device according to at least one embodiment of the present disclosure.

In a possible embodiment of the present disclosure, as shown in FIG. 4, the detection device further includes a prompting circuit 60 configured to send a prompt to the user after the image data about the to-be-detected object has been collected by image collection circuit 30. To be specific, prompting circuit 60 may be a buzzer which is configured to prompt the user that the image data has been collected successfully. Prompting circuit 60 may also be configured to broadcast to the user the visual information about the to-be-detected object acquired after processing the image data collected by image collection circuit 30, and the detection result of the to-be-detected object, e.g., broadcast the color value and the viscosity of the to-be-detected liquid via sound to the user.

Figure 5:
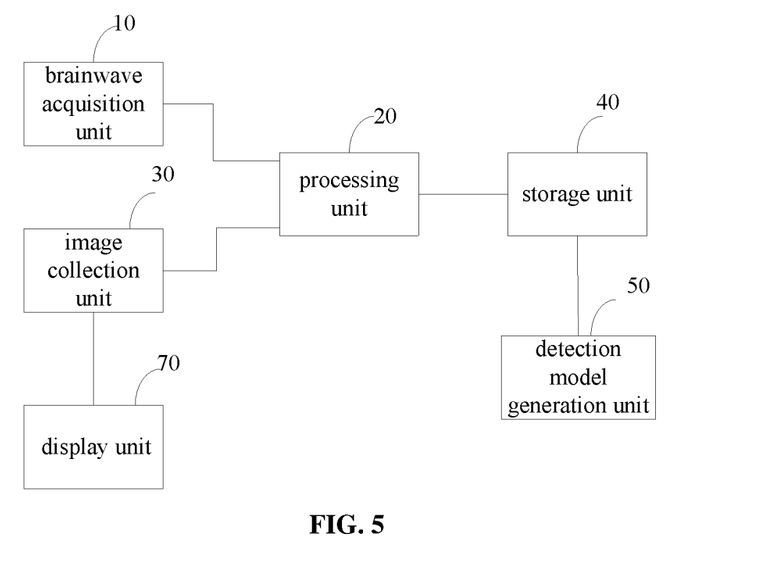
FIG. 5 is still yet another schematic view showing the detection device according to at least one embodiment of the present disclosure.

In a possible embodiment of the present disclosure, as shown in FIG. 5, the detection device further includes a display device 70 configured to display the visual information about the to-be-detected object, e.g., the color value and the transparency value of the to-be-detected liquid. For example, the display device may be a liquid crystal display panel or an organic light-emitting diode (OLED) display panel. In addition, display device 70 may also be configured to display the detection result of the to-be-detected object.

To be specific, the display device 70 may be arranged on the frame 11 and connected in a wired manner to image collection circuit 30. In addition, display device 70 may also be arranged at any convenient positions for users to watch and connected in a wireless manner to image collection circuit 30.

Figure 6:
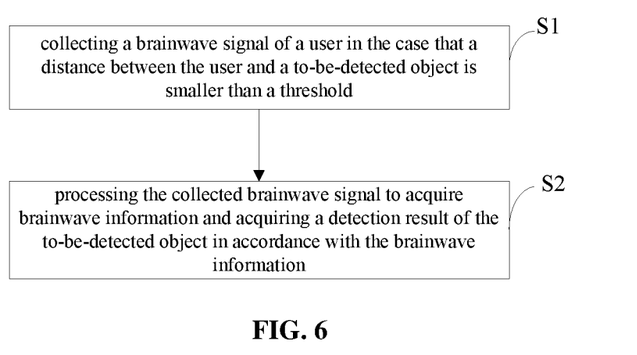
FIG. 6 is a flow chart of a detection method according to at least one embodiment of the present disclosure.

The present disclosure further provides in some embodiments a detection method which, as shown in FIG. 6, includes: Step S1 of collecting a brainwave signal of a user in the case that a distance between the user and a to-be-detected object is smaller than a threshold; and Step S2 of processing the collected brainwave signal to acquire brainwave information and acquiring a detection result of the to-be-detected object in accordance with the brainwave information. The brainwave information includes at least one of olfactory information and gustatory information of the user. The threshold may be set as 5 to 10 cm.

The detection method may be applied to the above-mentioned detection device. According to the detection method in the embodiments of the present disclosure, the brainwave signal of the user is collected in the case that the distance between the user and the to-be-detected object is smaller than the threshold, then the collected brainwave signal is processed so as to acquire the brainwave information, and then the detection result of the to-be-detected object is acquired in accordance with the brainwave information. Through this method, it is possible to acquire a detection result of the to-be-detected object in the case that the user wearing the detection device moves close to the to-be-detected object.

In a possible embodiment of the present disclosure, the detection method further includes: collecting image data about the to-be-detected object; and processing the image data to acquire visual information about the to-be-detected object, and acquiring the detection result of the to-be-detected object in accordance with the visual information and the brainwave information.

In a possible embodiment of the present disclosure, the step of acquiring the detection result of the to-be-detected object in accordance with the visual information and the brainwave information includes inputting the visual information and the brainwave information into a detection model acquired in advance, so as to acquire the detection result of the to-be-detected object.

In a possible embodiment of the present disclosure, the detection method further includes a step of generating the detection model, and the step of generating the detection model includes: acquiring training data, the training data including a plurality of detection results and a feature of the detection model corresponding to each detection result, the feature including olfactory neuron brainwave information, gustatory neuron brainwave information and visual information of the user collected in the case that the distance between the user and the to-be-detected object is smaller than the threshold; estimating a weight value of the feature of the detection model in accordance with the training data; and generating the detection model in accordance with the estimated weight value.

Figure 7:
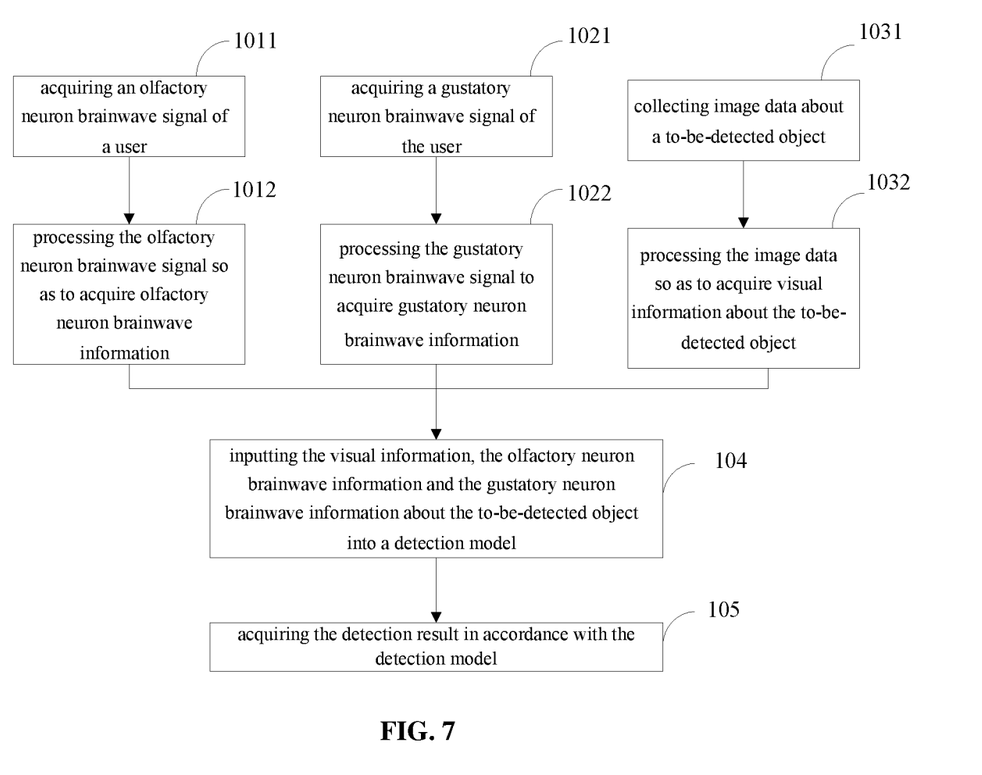
FIG. 7 is another flow chart of the detection method according to at least one embodiment of the present disclosure.

As shown in FIG. 7, the detection method may specifically include: Step 1011 of acquiring an olfactory neuron brainwave signal of the user; and Step 1012 of processing the olfactory neuron brainwave signal so as to acquire the olfactory neuron brainwave information. To be specific, a feature of the olfactory neuron brainwave signal may be extracted and then inputted into an olfaction detection model acquired in advance, so as to acquire the olfactory neuron brainwave information. The olfaction detection model may be acquired through training with a huge number of training data.

In addition, the detection device may further include: Step 1021 of acquiring a gustatory neuron brainwave signal of the user; and Step 1022 of processing the gustatory neuron brainwave signal so as to acquire the gustatory neuron brainwave information. To be specific, a feature of the gustatory neuron brainwave signal may be extracted and then inputted into a gustation detection model acquired in advance, so as to acquire the olfactory neuron brainwave information. The gustation detection model may be acquired through training with a huge number of training data.

In addition, the detection method may further include: Step 1031 of collecting image data about the to-be-detected object; and Step 1032 of processing the image data so as to acquire the visual information about the to-be-detected object.

In addition, the detection method may further include: Step 104 of inputting the visual information, the olfactory neuron brainwave information and the gustatory neuron brainwave information about the to-be-detected object into the detection model; and Step 105 of acquiring the detection result in accordance with the detection model.

During the implementation, in the case that the to-be-detected object is wine, the detection model may be expressed through the following equation $$p(\text{quality}|\text{parameter}) = \alpha_1 \times p_1(\text{quality}|\text{parameter}) + \alpha_2 \times p_2(\text{quality}|\text{parameter}) + \alpha_3 \times p_3(\text{quality}|\text{parameter}) \quad (1)$$

where p represents the detection result (the detection result may be mapped onto a wine quality parameter table acquired in advance, and the wine quality parameter table may include such parameters as odor types, vintages and alcohol contents, i.e., it is able to obtain the parameters of the wine directly through the detection result), $p_1$ represents a value of the olfactory neuron brainwave information acquired through extracting and analyzing an olfactory neuron brainwave signal, $p_2$ represents a value of the gustatory neuron brainwave information acquired through extracting and analyzing a gustatory neuron brainwave signal, $p_3$ represents a value of the visual information acquired through analyzing the image data collected by the image collection circuit (including the color value, the transparency value and the viscosity of the wine), $\alpha_1$ represents a weight value of $p_1$, $\alpha_2$ is a weight value of $p_2$, $\alpha_3$ is a weight value of $p_3$. $\alpha_1$, $\alpha_2$ and $\alpha_3$ are used to adjust influence coefficients of $p_1$, $p_2$ and $p_3$ respectively, and their values vary with the individual and are acquired by a particular subject through multiple trainings. For example, after a specific sommelier has smelt and tasted different types of wines for many times, the detection results and the values of $p_1$, $p_2$ and $p_3$ corresponding to each detection result may be recorded, so as to acquire a plurality of sets of training data. Then, the values of $\alpha_1$, $\alpha_2$ and $\alpha_3$ of the detection model may be estimated in accordance with training data, and the detection model may be generated in accordance with the estimated weight values. In order to improve the accuracy of the detection model, a huge number of training data acquired by a plurality of sommeliers may be used to train the detection model. The more the training data and the greater the number of sommeliers, the more precise the detection model becomes.

Different detection models may be established with respect to different to-be-detected objects. In the case that the to-be-detected objet is not wine, a huge number of training data may be acquired again, so as to train the detection model and estimate the weight values of the features of the detection model.

The above are merely the alternative embodiments of the present disclosure. A person skilled in the art may make further modifications and improvements without departing from the principle of the present disclosure, and these modifications and improvements shall also fall within the scope of the present disclosure.

It should be appreciated that, units and steps described in the embodiments of the present disclosure may be implemented in the form of electronic hardware, or a combination of a computer program and the electronic hardware. Whether or not these functions are executed by hardware or software depends on specific applications or design constraints of the technical solution. Different methods may be adopted with respect to the specific applications so as to achieve the described functions, without departing from the scope of the present disclosure.

It should be further appreciated that, for convenience and clarification, operation procedures of the system, device and units described hereinabove may refer to the corresponding procedures in the method embodiment, and thus will not be particularly defined herein.

It should be further appreciated that the device and method disclosed herein may be implemented in many other ways. For example, the embodiments for the device are merely for illustrative purposes, and the modules or units are provided merely on the basis of their logic functions. During the actual application, some modules or units may be combined together or integrated into another system. Alternatively, some functions of the module or units may be omitted or not executed. In addition, the coupling connection, direct coupling connection or communication connection between the modules or units may be implemented via interfaces, and the indirect coupling connection or communication connection between the modules or units may be implemented in an electrical or mechanical form or in any other form.

The units may be, or may not be, physically separated from each other. The units for displaying may be, or may not be, physical units, i.e., they may be arranged at an identical position, or distributed on a plurality of network elements. Parts or all of the units may be selected in accordance with the practical need, so as to achieve the purpose of the present disclosure.

In addition, the functional units in the embodiments of the present disclosure may be integrated into a processing circuit, or the functional units may exist independently, or two or more functional units may be combined together.

In the case that the functional units are implemented in a software form and sold or used as a separate product, they may be stored in a computer-readable medium. Based on this, the technical solutions of the present disclosure, partial or full, or parts of the technical solutions of the present disclosure contributing to the related art, may appear in the form of software products, which may be stored in a storage medium and include several instructions so as to enable computer equipment (a personal computer, a server or network equipment) to execute all or parts of the steps of the method according to the embodiments of the present disclosure. The storage medium includes any medium capable of storing therein program codes, e.g., a universal serial bus (USB) flash disk, a mobile hard disk (HD), a read-only memory (ROM), a random access memory (RAM), a magnetic disk or an optical disk.

Unless otherwise defined, such words as "one" or "one of" are merely used to represent the existence of at least one member, rather than to limit the number thereof. For example, such words as "a compound" or "at least one compound" may include a plurality of compounds, e.g., a mixture thereof.

The word "illustrative" merely refers to an example or instance, and any "illustrative" embodiment shall not be necessarily understood as a preferred embodiment, or being advantageous over any other embodiments, and/or excluding a combination of the features from the other embodiments.

The word "possible" refers to the feature involved in a certain embodiment is not provided in the other embodiment. Any specific embodiment of the present disclosure may include a plurality of "possible" features, in the case of no conflict.

Each embodiment in the present disclosure may be described in the form of a certain range. It should be appreciated that, the description in the form of the certain range is merely for convenience and clarification, but shall not be construed as limiting the scope of the present disclosure. Hence, the range shall be deemed as including all possible sub-ranges as well as any single value within the range, regardless of a width of the range. For example, the description "within the range of 1 to 6: shall be deemed as including such sub-ranges as "the range of 1 to 3", "the range of 1 to 4", "the range of 2 to 4", "the range of 2 to 6", "the range of 3 to 6", and any single value within the range, e.g., 1, 2, 3, 4, 5 and 6.

In the case that a specific numerical range is specified, it shall include all numbers (fractional or integral numbers) within the numerical range. Such expressions as "within the range of a first number to a second number" or "ranging from a first number to a second number" are intended to include the first number, the second number and any fractional and integral numbers between the first number and the second number.

It should be further appreciated that, for clarification, some features are separately described in several embodiments, but they may also be combined in a single embodiment. Also, the features described in a single embodiment may also be described separately, or in any appropriate combinations, in the other embodiments. Some features described in a certain embodiment shall not be deemed as necessary features for the embodiment, unless the embodiment is unfeasible without these features.

Although the present disclosure has been described in detail in reference to some specific embodiments, it is needless to say for skilled persons in the art that many modifications, substitutions, and changes are obvious. Therefore it is intended that all these modifications, substitutions, and changes are all falling into the scope of the present disclosure.

The above are merely the preferred embodiments of the present disclosure, but the present disclosure is not limited thereto. Obviously, a person skilled in the art may make further modifications and improvements without departing from the spirit of the present disclosure, and these modifications and improvements shall also fall within the scope of the present disclosure.

What is claimed is:

1. A detection device, comprising:
    a brainwave acquisition circuit configured to collect a brainwave signal of a user;
    a processing circuit configured to process the brainwave signal to acquire brainwave information, and acquire a detection result of a to-be-detected object by the detection device in accordance with the brainwave information; and
    an image collection circuit in communication with the processing circuit and configured to collect image data about the to-be-detected object,
    wherein the brainwave information comprises at least one of olfactory information and gustatory information of the user; and
    wherein the processing circuit is further configured to process the image data collected by the image collection circuit to acquire visual information about the to-be-detected object, and acquire the detection result of the to-be-detected object in accordance with the visual information and the brainwave information.

2. The detection device according to claim 1, further comprising a storage-device configured to store therein a detection model, wherein the processing circuit is further configured to input the visual information and the brainwave information into the detection model, so as to acquire the detection result of the to-be-detected object.

3. The detection device according to claim 2, further comprising a detection model generation circuit configured to:
    acquire training data, the training data comprising a plurality of detection results and a feature of the detection model corresponding to each detection result of the plurality of detection results, the feature comprising olfactory neuron brainwave information, gustatory neuron brainwave information and visual information of the user collected in a case that a distance between the user and the to-be-detected object is smaller than a threshold;
    estimate a weight value of the feature of the detection model in accordance with the training data; and
    generate the detection model in accordance with the weight value that was estimated.

4. The detection device according to claim 1, wherein the image collection circuit comprises:
    a light transmitter configured to connect with the processing circuit and transmit a light beam toward the to-be-detected object; and
    an optical processor configured to detect at least one of a light beam acquired after the light beam transmitted by the light transmitter passes through the to-be-detected object and a light beam acquired after the light beam from the light transmitter is reflected by the to-be-detected object, so as to acquire the visual information about the to-be-detected object.

5. The detection device according to claim 1, further comprising a prompting circuit configured to send a prompt to the user after the image data about the to-be-detected object has been collected by the image collection circuit.

6. The detection device according to claim 1, further comprising a display circuit configured to display the visual information about the to-be-detected object.

7. The detection device according to claim 1, wherein the brainwave acquisition circuit comprises a frame and a plurality of detection electrodes arranged on the frame.

8. The detection device according to claim 7, wherein the image collection circuit is arranged on the frame and connected in a wired or wireless manner to the processing unit.

9. The detection device according to claim 1, wherein the image collection circuit comprises:
    a light transmitter configured to connect with the processing circuit and transmit a light beam toward the to-be-detected object; and
    an optical processor configured to detect at least one of a light beam acquired after the light beam transmitted by the light transmitter passes through the to-be-detected object and a light beam acquired after the light beam from the light transmitter is reflected by the to-be-detected object, so as to acquire the visual information about the to-be-detected object.

10. The detection device according to claim 7, wherein a distribution pattern of the plurality of detection electrodes on the frame corresponds to positions of olfactory neurons and gustatory neurons in a user brain.

11. The detection device according to claim 7, wherein the frame is a helmet.

12. A detection method, comprising:
    collecting a brainwave signal of a user in a case that a distance between the user and a to-be-detected object is smaller than a threshold; and
    processing the brainwave signal to acquire brainwave information and acquiring a detection result of the to-be-detected object in accordance with the brainwave information,
    wherein the brainwave information comprises at least one of olfactory information and gustatory information of the user, and wherein the detection method further comprises:
  collecting image data about the to-be-detected object; and
  processing the image data to acquire visual information about the to-be-detected object, and acquiring the detection result of the to-be-detected object in accordance with the visual information and the brainwave information.

13. The detection method according to claim 12, wherein the acquiring the detection result of the to-be-detected object in accordance with the visual information and the brainwave information comprises inputting the visual information and the brainwave information into a detection model acquired in advance, so as to acquire the detection result of the to-be-detected object.

14. The detection method according to claim 13, further comprising generating the detection model, wherein the generating the detection model comprises:
  acquiring training data, the training data including a plurality of detection results and a feature of the detection model corresponding to each detection result of the plurality of detection results, the feature comprising olfactory neuron brainwave information, gustatory neuron brainwave information and visual information of the user collected in a case that the distance between the user and the to-be-detected object is smaller than the threshold;
  estimating a weight value of the feature of the detection model in accordance with the training data; and
  generating the detection model in accordance with the weight value that was estimated.

15. A non-transitory computer-readable storage medium storing therein a computer program which is executed by a processor so as to implement a detection method, comprising
  collecting a brainwave signal of a user in a case that a distance between the user and a to-be-detected object is smaller than a threshold; and
  processing the brainwave signal to acquire brainwave information and acquiring a detection result of the to-be-detected object in accordance with the brainwave information,
  wherein the brainwave information comprises at least one of olfactory information and gustatory information of the user, and
  wherein the detection method further comprises:
    collecting image data about the to-be-detected object; and
    processing the image data to acquire visual information about the to-be-detected object, and acquiring the detection result of the to-be-detected object in accordance with the visual information and the brainwave information.

16. The non-transitory computer-readable storage medium according to claim 15, wherein acquiring the detection result of the to-be-detected object in accordance with the visual information and the brainwave information comprises inputting the visual information and the brainwave information into a detection model acquired in advance, so as to acquire the detection result of the to-be-detected object.

17. The non-transitory computer-readable storage medium according to claim 16, wherein the detection method further comprises generating the detection model,
  wherein the generating the detection model comprises:
    acquiring training data, the training data including a plurality of detection results and a feature of the detection model corresponding to each detection result of the plurality of detection results, the feature comprising olfactory neuron brainwave information, gustatory neuron brainwave information and visual information of the user collected in a case that the distance between the user and the to-be-detected object is smaller than the threshold;
    estimating a weight value of the feature of the detection model in accordance with the training data; and
    generating the detection model in accordance with the estimated weight value.

* * * * *